US00PP08380P

United States Patent [19]

Warriner et al.

[11] Patent Number: Plant 8,380

[45] Date of Patent: Sep. 21, 1993

[54] ROSE PLANT JACFIDD

[75] Inventors: William A. Warriner, Tustin; Keith W. Zary, Thousand Oaks, both of Calif.

[73] Assignee: Bear Creek Gardens, Inc., Medford, Oreg.

[21] Appl. No.: 796,030

[22] Filed: Nov. 21, 1991

[51] Int. Cl.[5] ..... A01H 5/00

[52] U.S. Cl. ..... Plt./24

[58] Field of Search ..... Plt./24, 15, 8.2

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

A new floribunda rose from a cross of the variety MINzco with the variety JACyim, is characterized by its large, unusual obovate shaped flower petals, its ease of reproduction with softwood cuttings, and excellent disease resistance.

1 Drawing Sheet

The present invention relates to a new and distinct variety of rose plant of the Floribunda class which was originated by us by crossing the variety MINzco, with the variety JACyim, U.S. Plant Pat. No. 7,127.

The primary objective of this breeding was to produce a new rose variety having the larger petals of the variety MINzco coupled with the excellent disease resistance of JACyim. The objective was substantially achieved along with other desirable improvements as evidenced by the following unique combination of characteristics which are outstanding in the new variety and which distinguish it from its parents, as well as from all other varieties of which I am aware:

1. Bright yellow, moderately scented flowers;
2. Unusual obovate shaped petals;
3. Leathery dark green, glossy, disease resistant leaves;
4. Ease of production as softwood cuttings.

Asexual reproduction of this new variety by budding and by softwood cuttings, as performed at Wasco and Somis, Calif., shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
- *Seed parent.*—MINzco.
- *Pollen parent.*—JACyim.

Classification:
- *Botanical.*—*Rosa hybrida.*
- *Commercial.*—Floribunda.

FLOWER

Observations made from specimens grown Somis, Calif. in April–June of 1991.

Blooming habit: Recurrent.

Bud:

- *Size.*—1 inch when the petals start to unfurl.
- *Form.*—Long, pointed ovoid.
- *Color.*—When sepals first divide, bud color is Yellow Group 8A. When half blown, the upper sides of the petals are Yellow Group 8A; and the lower sides of the petals are Yellow Group 8A.
- *Sepals.*—Color: Green Group 138C. Surface texture: Covered in fine hairs. There are three lightly appendaged sepals. There are two unappendaged sepals with hairy edges.
- *Receptacle.*—Color: Green Group 143A. Shape: Funnel. Size: Medium, $\frac{3}{8}'' \times \frac{3}{8}''$. Surface: Hairy.
- *Peduncle.*—Length: Short, 1". Surface: Smooth and covered with fine hairs. Color: Bronzy.
- *Strength.*—Strength: Stiff, erect.

Bloom:
- *Size.*—Medium. Average open size is 3 inches.
- *Borne.*—Several together, in flat clusters.
- *Stems.*—Medium, strong, 10–12".
- *Form.*—When first open: Cupped. Permanence: Flattens.
- *Petalage.*—Number of petals under normal conditions: 30–35.
- *Color.*—The upper side of the petals is Yellow Group 8A. The reverse side of the petals is Yellow Group 8A. The base of petals is Yellow Group 8A. The major color on the upper side is yellow Group 8A.
- *Variegations.*—None
- *Discoloration.*—At the end of the first day: None. At the end of the third day, gradual fading toward Yellow Group 8B then to 8C.
- *Fragrance.*—Moderate.

Petals:
- *Texture.*—Thick.
- *Shape.*—Obovate.
- *Form.*—Edges slightly quilled.
- *Arrangement.*—Imbricated, with a few petaloids in the center.
- *Persistence.*—Drop off cleanly.
- *Lastingness.*—On the plant: Fair, 4–5 days.

As a cut flower: Fair, 5–6 days.

Reproductive parts:
- *Anthers.*—Size: Medium. Quantity: Many. Color: Yellow. Arrangement: Regular around styles, mixed with occasional petaloids.
- *Filaments.*—Color: Reddish brown.

*Pollen.*—Color: Gold-Yellow.
*Styles.*—Color: Reddish.
*Stigmas.*—Color: Greenish-white.

Form: Bush.

Growth: Vigorous; upright; branching; compact.

Foliage:
*Number of leaflets on normal mid-stem leaves.*—
*Size.*—Medium, $4\frac{1}{2}'' \times 3\frac{1}{2}''$.
*Quantity.*—Abundant.
*Color.*—New foliage: Reddish. Old foliage: Dark glossy green.

Leaflets:
*Shape.*—Pointed oval.
*Texture.*—Upper side: Leathery, glossy.
*Edge.*—Serrated.
*Serration.*—Single.
*Petiole rachis.*—Color: Green.
*Petiole underside*—Rough with prickles.
*Stipules.*—Medium, $\frac{3}{4}''$, bearded.
*Disease resistance.*—Resistant to mildew and rust under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Medium, hooked downward.
*Color when young.*—Red.

Small prickles:
*Quantity.*—On main stalks: None. On laterals: None.

We claim:

1. A new and distinct variety of rose plant of the Floribunda class, substantially as herein shown and described, characterized particularly as to novelty by the unique combination of its ease of production by softwood cuttings, its dark green, glossy, leathery and disease resistant foliage, its bright yellow moderately scented flowers and its large, unusual obovate shaped petals.

* * * * *

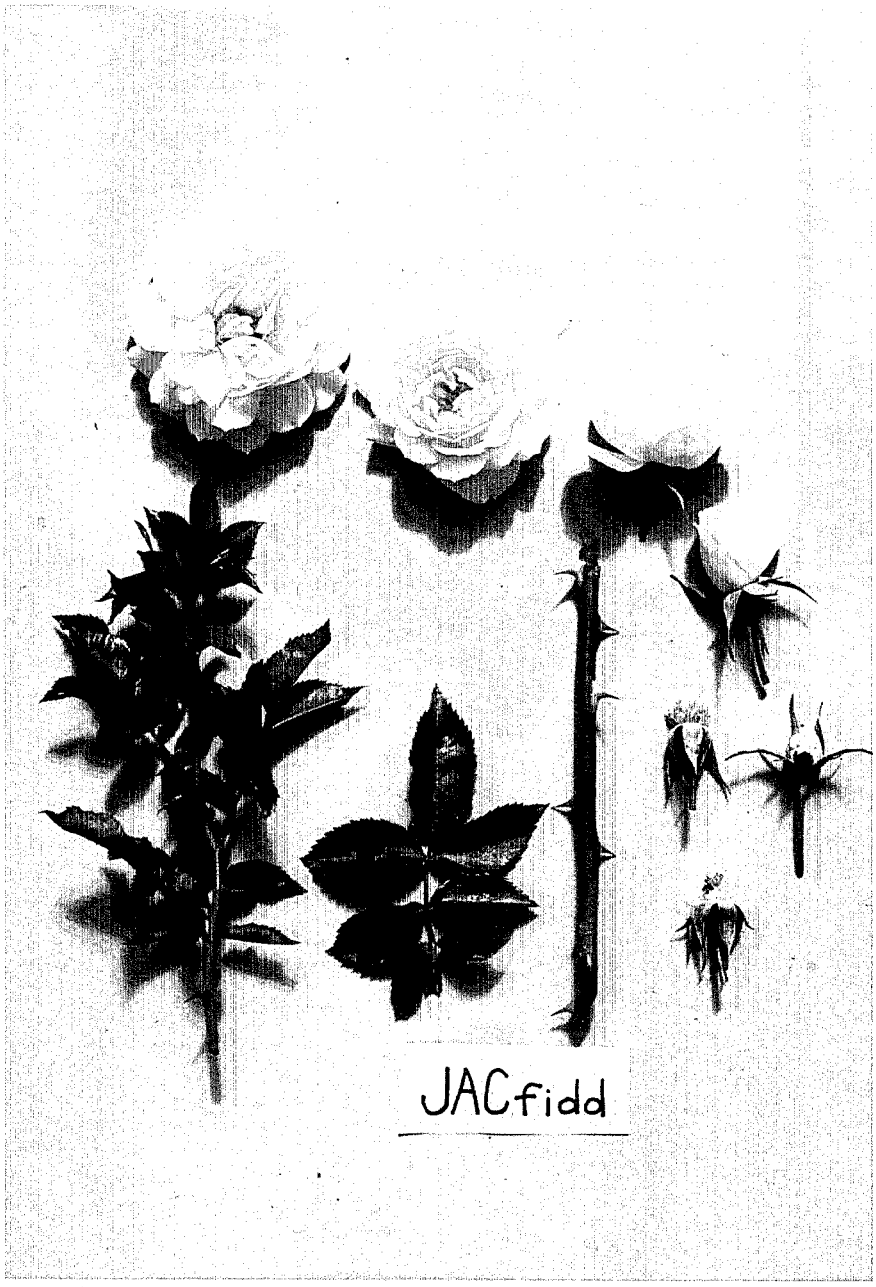
JACfidd